United States Patent [19]
Dixon et al.

[11] Patent Number: 6,093,397
[45] Date of Patent: Jul. 25, 2000

[54] AMYLOID PRECURSOR PROTEIN PROTEASE

[75] Inventors: Eric P Dixon, Apex, N.C.; Edward M. Johnstone; Sheila P. Little, both of Indianapolis, Ind.

[73] Assignee: Eli Lilly and Company, Indianapolis, Ind.

[21] Appl. No.: 08/930,188

[22] PCT Filed: Apr. 2, 1996

[86] PCT No.: PCT/US96/04294

§ 371 Date: Oct. 2, 1997

§ 102(e) Date: Oct. 2, 1997

[87] PCT Pub. No.: WO96/31122

PCT Pub. Date: Oct. 10, 1996

Related U.S. Application Data

[63] Continuation of application No. 08/416,257, Apr. 4, 1995, abandoned.

[51] Int. Cl.[7] .............................. A61K 38/48; C12N 9/48; C12N 1/20; C07H 21/04

[52] U.S. Cl. .................................... 424/94.64; 424/78.02; 424/94.62; 435/69.1; 435/212; 435/213; 435/219; 435/226; 435/252.3; 435/320.1

[58] Field of Search .................................. 435/212, 213, 435/226, 219, 69.1, 252.3, 320.1, 252.33; 536/23.2, 23.5; 424/78.02, 94.62, 94.64; 935/14, 29, 32, 70, 73

[56] References Cited

PUBLICATIONS

Hansson et al., J. Biol. Chem. 269(30):19420–26, Jul.29, 1994.
Nelson et al. J. Neurochem. 61, 567–577 (1993).
Skytt et al. Biochem. Biophys. Res. Comm. 211(2): 586–589, Jun. 15, 1995.

*Primary Examiner*—Ponnathapu Achutamurhy
*Assistant Examiner*—Tekchand Saidha
*Attorney, Agent, or Firm*—Alexander Wilson; Paul J. Gaylo

[57] ABSTRACT

This invention describe a novel human amyloid precursor protein protease; nucleic acids encoding the protease; and methods employing the protease, as well as methods employing the nucleic acids encoding the protease.

16 Claims, No Drawings

AMYLOID PRECURSOR PROTEIN PROTEASE

This application is a 371 of PCT/US96/04294, filed Apr. 2, 1996, which is a continuation of U.S. Ser. No. 08/416,257, filed Apr. 4, 1995, now abandoned.

Alzheimer's disease is a degenerative disorder of the human brain. Clinically, it appears as a progressive dementia. Its histopathology is characterized by degeneration of neurons, gliosis, and the abnormal deposition of proteins in the brain. Proteinaceous deposits (called "amyloid") appear as neurofibrillary tangles, amyloid plaque cores, and amyloid of the congophilic angiopathy. [For a review, see, D. J. Selkoe, *Neuron*, 6:487–498 (1991)]

While there is no general agreement as to the chemical nature of neurofibrillary tangles, the major constituent of both the amyloid plaque cores and the amyloid of the congophilic angiopathy has been shown to be a 4500 Dalton protein originally termed β-protein or amyloid A4. Throughout this document this protein is referred to as β-amyloid peptide or protein.

β-Amyloid peptide is proteolytically derived from a transmembrane protein, the amyloid precursor protein. Different splice forms of the amyloid precursor protein are encoded by a widely expressed gene. see, e.g., K. Beyreuther and B. Müller-Hill, *Annual Reviews in Biochemistry*, 58:287–307 (1989). The most abundant form of amyloid precursor protein found in the human brain contains 695 amino acid residues and is designated as APP 695. At least three other forms do exist, however, these being given the names APP 714, APP 751, and APP 770. Tanzi, et al., *Nature (London)*, 351:328 (1988); Ponte, et al., *Nature (London)*, 331:525 (1988); Kitaguchi, et al., *Nature (London)*, 331:530 (1988).

The different length isoforms arise from alternative splicing from a single amyloid precursor protein gene located on chromosome 21. Goldgaber, et al., *Science*, 235:877 (1987).

APP 751 and APP 770 contain a 56 amino acid Kunitz imhibitor domain, which shares 40% homology with bovine pancreatic trypsin inhibitor. Both of these forms of amyloid pancreatic trypsin inhibitor. Both of these forms of amyloid precursor protein have protease inhibitory activity. Kitaguchi, et al., supra.

Studies have also been performed to examine if changes in the relative amounts of the different forms of amyloid precursor protein are responsible for amyloid accumulation. The results of such studies have been equally confusing, but have generally supported the conclusion that the relative expression levels of the Kunitz domain containing amyloid precursor proteins are elevated in Alzheimer's disease. Johnson, et al., *Science*, 248:854 (1990).

Recent studies have shown that amyloid precursor protein fragments extending from the N-terminus of β-amyloid peptide to the C-terminus of the full length amyloid precursor protein (the "C-100 fragment") are also capable of aggregation in vitro and in transfected cells. Dyrks, et al., *EMBO Journal*, 7:949 (1988); Wolf, et al., *EMBO Journal*, 9:2079 (1990).

β-amyloid peptide consists, in its longest forms, of 42 or 43 amino acid residues. J. Kang, et al., *Nature (London)*, 325:733–736 (1987). These peptides, however, vary as to their amino-termini. C. Hilbich, et al., *Journal of Molecular Biology*, 218:149–163 (1991).

The enzymes responsible for the normal, non-pathological processing of amyloid precursor protein have been termed "secretases". It is believed that the net pathological accumulation of β-amyloid peptide is controlled by the relative activities of the pathologic and physiologic pathways of amyloid precursor protein.

Because senile plaques are invariably surrounded by dystrophic neurites, it was proposed early that β-amyloid peptide is involved in the loss of neuronal cells that occurs in Alzheimer's disease. Bruce Yankner and co-workers were the first to demonstrate that synthetic β-amyloid peptide could be neurotoxic in vitro and in vivo. B. A. Yankner, et al., *Science*, 245:417 (1989); See, also, N. W. Kowall, et al., *Proceedinas of the National Academy of Sciences, U.S.A.*, 88:7247 (1991).

While many of the peptides which result from the processing of amyloid precursor protein have been identified, the proteases responsible for this processing remain unidentified for the most part.

In addition to Alzheimer's disease, Down's syndrome is also characterized by an accumulation of β-amyloid peptide. In patients suffering from Down's syndrome the β-amyloid peptide is the primary constituent of senile plaques and cerebrovascular deposits.

Because of the debilitating effects of Alzheimer's disease, Down's syndrome, and these other conditions associated with amyloidogenic peptides and proteins there continues to exist a need for effective treatments. This invention provides a novel serine protease which is believed to be involved in the processing or clearance of amyloid precursor protein to form β-amyloid peptide. This protease, therefore, is useful in the design and testing of compounds having utility in the treatment or prevention of a condition associated with β-amyloid peptide, especially Alzheimer's Disease.

This invention provides an isolated amino acid compound useful as a human amyloid precursor protein protease, said compound comprising the amino acid sequence

```
Met Ala Arg Ser Leu Leu Leu Pro Leu Gln Ile Leu Leu
 1                5                    10
Leu Ser Leu Ala Leu Glu Thr Ala Gly Glu Glu Ala Gln
         15                20                    25
Gly Asp Lys Ile Ile Asp Gly Ala Pro Cys Ala Arg Gly
                 30                    35
Ser His Pro Trp Gln Val Ala Leu Leu Ser Gly Asn Gln
 40                   45                    50
Leu His Cys Gly Gly Val Leu Val Asn Glu Arg Trp Val
         55                    60                    65
Leu Thr Ala Ala His Cys Lys Met Asn Glu Tyr Thr Val
                 70                    75
His Leu Gly Ser Asp Thr Leu Gly Asp Arg Arg Ala Gln
 80                   85                    90
Arg Ile Lys Ala Ser Lys Ser Phe Arg His Pro Gly Tyr
             95                    100
Ser Thr Gln Thr His Val Asn Asp Leu Met Leu Val Lys
105                   110                   115
Leu Asn Ser Gln Ala Arg Leu Ser Ser Met Val Lys Lys
         120                   125                   130
Val Arg Leu Pro Ser Arg Cys Glu Pro Pro Gly Thr Thr
                 135                   140
Cys Thr Val Ser Gly Trp Gly Thr Thr Thr Ser Pro Asp
     145                   150                   155
```

-continued

```
Val Thr Phe Pro Ser Asp Leu Met Cys Val Asp Val Lys
            160                 165

Leu Ile Ser Pro Gln Asp Cys Thr Lys Val Tyr Lys Asp
170                 175                 180

Leu Leu Glu Asn Ser Met Leu Cys Ala Gly Ile Pro Asp
            185                 190                 195

Ser Lys Lys Asn Ala Cys Asn Gly Asp Ser Gly Gly Pro
                200                 205

Leu Val Cys Arg Gly Thr Leu Gln Gly Leu Val Ser Trp
    210                 215                 220

Gly Thr Phe Pro Cys Gly Gln Pro Asn Asp Pro Gly Val
            225                 230

Tyr Thr Gln Val Cys Lys Phe Thr Lys Trp Ile Asn Asp
235                 240                 245

Thr Met Lys Lys His Arg
            250
``` hereinafter designated as SEQ ID NO:2.

The invention also provides an isolated nucleic acid compound that comprises a nucleic acid sequence which encodes for the amino acid compounds provided. Particularly this invention provides the isolated nucleic acid compound having the sequence This invention also provides assays for determining protein regions which are susceptible to cleavage by the human amyloid precursor protein proteases of the present invention.

In further embodiments this invention provides assays for determining the efficacy and adverse reaction profile of agents useful in the treatment or prevention of disorders associated with an excess or deficiency in the amount of human amyloid precursor protein protease present.

The terms and abbreviations used in this document have their normal meanings unless otherwise designated. For example "C" refers to degrees Celsius; "N" refers to normal or normality; "mmole" refers to millimole or millimoles; "g" refers to gram or grams; "ml" means milliliter or milliliters; "M" refers to molar or molarity; "µg" refers to microgram or micrograms; and "µl" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA

```
GAATTCCGGT TTTTTTTTTT TGAGGGTTTT GTGTTTCTTT ATTTGTTTTG GTTTTAGGTC    60

TTTACCAATT TGATTGGTTT ATCAACAGGG CATGAGGTTT AAATATATCT TTGAGGAAAG   120

GTAAAGTCAA ATTTGACTTC ATAGGTCATC GGCGTCCTCA CTCCTGTGCA TTTTCTGTTG   180

GAAGCACACA GTTAATTAAC TCAGTGTGGC GTTAGCGATG CTTTTTCATG GTGTCATTTA   240

TCCACTTGGT GAACTTGCAG ACTTGAGTGT AGACTCCTGG GTCATTGGGT TGGCCGCAAG   300

GGAAAGTTCC CCAGGACACC AGACCTTGCA GGGTACCTCT GCACACCAAC GGTCCCCCTG   360

AGTCACCATT GCAGGCGTTT TTCTTGGAGT CGGGGATGCC AGCGCACAGC ATGGAATTTT   420

CCAGTAAGTC CTTGTAAACC TTCGTGCAGT CCTGGGGGA GATGAGCTTG ACATCCACGC    480

ACATGAGGTC AGAGGGAAAG GTCACATCTG GGCTCGTGGT AGTGCCCCAG CCGGAGACAG   540

TACAGGTGGT TCCAGGGGGT TCGCAGCGGG AGGGCAGCCT GACTTTCTTC ACCATGGATG   600

ACAGCCTGGC CTGGCTATTG AGCTTCACGA GCATGAGGTC ATTAACATGG GTCTGTGTGG   660

AGTAGCCGGG GTGGCGGAAT GACTTCGAGG CCTTGATCCT CTGAGCTCTC CTGTCGCCCA   720

GCGTATCACT GCCCAGGTGC ACGGTGTACT CATTCATCTT GCAGTGGGCG GCAGTGAGCA   780

CCCAGCGCTC ATTGACCAGG ACGCCTCCGC AGTGGAGCTG ATTGCCACTG AGCAGGGCCA   840

CCTGCCATGG GTGGGAGCCT CTTGCACATG GGGCGCCATC AATAATCTTG TCACCCTGGG   900

CTTCTTCTCC TGCAGTTTCC AAGGCTAAGG ATAGCAGTAA GATCTGCAGG GGCAGGAGAA   960

GGGATCTTGC CATGGTGCCC TGCTGAGCCG CTCAGGGGCT GCCAGGCGAG GAAGGGCCTC  1020

TCCTGCTGGA GCTCGAGAGG ATCTGATGTG ATCCAAGTTC CGACTTGGGC TGGCACACAC  1080

CGGAATTCC                                                         1089
``` which is hereinafter designated as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments (T. Maniatis, et al., *MOLECULAR CLONING: A LABORATORY MANUAL*, 1982, p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/cr followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., *MOLECULAR CLONING: A LABORATORY MANUAL,* (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "PCR" as used herein refers to the widely-known polymerase chain reaction employing a thermally-stable polymerase.

This invention provides the protein of SEQ ID NO:2, a human amyloid precursor protein. This protease is believed to be involved in the maturation of human amyloid precursor protein, especially that route of maturation which results in the formation of β-amyloid peptide.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See. e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City California) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids , the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished using standard deprotection procedures, such as with trifluoroacetic acid (TFA) in methylene chloride. Following completion of the synthesis, the peptides may be deprotected and cleaved from the resin with anhydrous hydrogen fluoride containing 10% m-cresol. Cleavage of the side chain protecting group(s) and of the peptide from the resin is carried out at zero degrees Celsius or below, preferably at about −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., Methods in Enzymology, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
|---|---|
| DH5α | F− (φ80dlacZΔM15), Δ(lacZYA-argF)U169 supE44, λ−, hsdR17($r_K^-$, $m_K^+$), recA1, endA1, gyrA96, thi-1, relA1 |
| HB101 | supE44, hsdS20($r_B^-$ $m_B^-$), recA13, ara-14, proA2 lacY1, galK2, rpsL20, xyl-5, mtl-1, mcrB, mrr |
| JM109 | recA1, e14−(mcrA), supE44, endA1, hsdR17($r_K^-$, $m_K^+$), gyrA96, relA1, thi-1, Δ(lac-proAB), F′[traD36, proAB+ lacI$^q$,lacZΔM15] |
| RR1 | supE44, hsdS20($r_B^-$ $m_B^-$), ara-14 proA2, lacY1, galK2, rpsL20, xyl-5, mtl-5 |
| X1776 | F−, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ− |
| 294 | endA, thi−, hsr−, hsm$_K^+$ (U.S. Pat. No. 4,366,246) |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra.

In addition to the strains of *E. coli* discussed supra, bacilli such as *Bacillus subtilis,* other enterobacteriaceae such as *Salmonella typhimurium* or *Serratia marcescans,* and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., Nature (London), 275:615 (1978); and Goeddel et al., Nature (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine- Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in *PROTEIN PURIFICATION: FROM MOLECULAR MECHANISMS TO LARGE SCALE PROCESSES*, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed in Table I

TABLE I

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| 293 | Human Embyronal Kidney | ATCC CRL 1573 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. A depiction of the plasmid phd is provided as FIG. 2 of this document. The phd series of plasmids functions most efficiently when introduced into a host cell which produces the ElA gene product, cell lines such as AV12-664, 293 cells, and others, described supra.

An especially preferred vector employed in this invention uses a transcriptional regulatory region from cytomegalovirus. This vector (pRc/CMV) is commercially available (Invitrogen Corporation, San Diego, Calif.) and is described in A. Akrigg, et al., *Virus Research*, 2:107–121 (1985). This vector contains a restriction endonuclease polylinker to allow rapid unidirectional insertion of the gene of interest.

Transformation of the mammalian cells can be performed by any of the known processes including, but not limited to, the protoplast fusion method, the calcium phosphate co-precipitation method, electroporation and the like. See. e.a., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomvces sp., the plasmid YRp7 (ATCC-40053), for example, is commonly used. See. e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructoklnase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec--hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II.

TABLE II

| Original Residue | Exemplary Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human amyloid precursor protein protease molecule may be produced using synthetic methodology. This synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See. e.g., *OLIGONUCLEOTIDE SYNTHESIS, A PRACTICAL APPROACH*, (M. J. Gait, ed., 1984).

The synthetic human amyloid precursor protein protease gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the hAPP protease molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence

```
GAAUUCCGGU UUUUUUUUUU UGAGGGUUUU GUGUUUCUUU AUUUGUUUUG GUUUUAGGUC    60

UUUACCAAUU UGAUUGGUUU AUCAACAGGG CAUGAGGUUU AAAUAUAUCU UUGAGGAAAG   120

GUAAAGUCAA AUUUGACUUC AUAGGUCAUC GGCGUCCUCA CUCCUGUGCA UUUUCUGUUG   180

GAAGCACACA GUUAAUUAAC UCAGUGUGGC GUUAGCGAUG CUUUUUCAUG GUGUCAUUUA   240

UCCACUUGGU GAACUUGCAG ACUUGAGUGU AGACUCCUGG GUCAUUGGGU UGGCCGCAAG   300

GGAAAGUUCC CCAGGACACC AGACCUUGCA GGGUACCUCU GCACACCAAC GGUCCCCUG    360

AGUCACCAUU GCAGGCGUUU UUCUUGGAGU CGGGGAUGCC AGCGCACAGC AUGGAAUUUU   420

CCAGUAAGUC CUUGUAAACC UUCGUGCAGU CCUGGGGGA GAUGAGCUUG ACAUCCACGC    480

ACAUGAGGUC AGAGGGAAAG GUCACAUCUG GGCUCGUGGU AGUGCCCCAG CCGGAGACAG   540

UACAGGUGGU UCCAGGGGGU UCGCAGCGGG AGGGCAGCCU GACUUUCUUC ACCAUGGAUG   600

ACAGCCUGGC CUGGCUAUUG AGCUUCACGA GCAUGAGGUC AUUAACAUGG GUCUGUGUGG   660

AGUAGCCGGG GUGGCGGAAU GACUUCGAGG CCUUGAUCCU CUGAGCUCUC CUGUCGCCCA   720

GCGUAUCACU GCCCAGGUGC ACGGUGUACU CAUUCAUCUU GCAGUGGGCG GCAGUGAGCA   780

CCCAGCGCUC AUUGACCAGG ACGCCUCCGC AGUGGAGCUG AUUGCCACUG AGCAGGGCCA   840

CCUGCCAUGG GUGGGAGCCU CUUGCACAUG GGGCGCCAUC AAUAAUCUUG UCACCCUGGG   900

CUUCUUCUCC UGCAGUUUCC AAGGCUAAGG AUAGCAGUAA GAUCUGCAGG GGCAGGAGAA   960

GGGAUCUUGC CAUGGUGCCC UGCUGAGCCG CUCAGGGGCU GCCAGGCGAG GAAGGGCCUC  1020

UCCUGCUGGA GCUCGAGAGG AUCUGAUGUG AUCCAAGUUC CGACUUGGGC UGGCACACAC  1080

CGGAAUUCC                                                         1089
``` hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3, a complementary sequence of either SEQ ID NO:1 or SEQ ID NO:3, or a fragment thereof, and which is at least 18 base pairs in length, and which will selectively hybridize to human genomic DNA or messenger RNA encoding a human glutamate receptor, is provided. Preferably, the 18 or more base pair compound is DNA.

The term "selectively hybridize" as used herein may refer to either of two situations. In the first such embodiment of this invention, the nucleic acid compounds described supra hybridize to a human amyloid precursor protein protease under more stringent hybridization conditions than these same nucleic acid compounds would hybridize to an analogous protease in another species, e.g. murine or primate. In the second such embodiment of this invention, these probes hybridize to the hAPP protease under more stringent hybridization conditions than other related compounds, including nucleic acid sequences encoding other serine proteases.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1.

The nucleic acid compounds encoding the human amyloid precursor protein protease were prepared by probing messenger (mRNA) isolated from human brain tissue, superior frontal gyrus. The probes employed were designed from conserved regions in known serine proteases. One primer employed in this cloning contained the following sequence:

GTG(A/C)TGACAGCTGCCCACTG which is hereinafter referred to as SEQ ID NO:7. Another primer sequence employed contained the following sequence:

CAGCT(G/T)CAGCAGCATGATGTC which is hereinafter referred to as SEQ ID NO:8.

From the mRNA so isolated cDNA was prepared using standard commercially available kits and protocols. After the synthesis of this first strand, multiple copies of this cDNA were prepared using PCR technology. The products of the PCR process were then electrophoretically separated on a Daiichi gel and those fragments having the expected were excised, and the DNA was extracted using standard techniques.

The full-length clone of the human amyloid precursor protein protease was then isolated from a commercially available human lung cDNA lambda gt10 library. The skilled practitioner understands that other readily available cDNA libraries may be used in the preparation of the nucleotides of this invention. After the full-length clone was isolated, it was sequenced using standard techniques to give the nucleic acid sequences described in this invention.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

A plasmid comprising the nucleic acids of the present invention is readily modified to construct expression vectors that produce human amyloid precursor protein protease in a variety of organisms, including, for example, *E. coli*, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, *CURRENT PROTOCOLS IN MOLECULAR BIOLOGY*, 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for E. coli can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and E. coli cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is AV12. The preferred vector for expression is one which comprises SEQ ID NO:1. Another preferred host cell for this method is E. coli. An especially preferred expression vector in E. coli is one which comprises SEQ ID NO:1. Transformed host cells may be cultured under conditions well known to skilled artisans such that SEQ ID NO:2 is expressed, thereby producing human amyloid precursor protein protease in the recombinant host cell.

The ability of the human amyloid precursor protein protease to cleave the appropriate substrate is essential in the development of a multitude of indications. The development of agents which interfere or inhibit this cleavage is, therefore, important in the development of thereapeutic agents effective in the treatment or prevention of conditions such as Alzheimer's Disease.

As used herein, the term "amyloid precursor protein substrate" or "APP substrate" refers to full length amyloid precursor protein, whether derived by isolation or purification from a biological source or by expression of a cloned gene encoding amyloid precursor protein or its analogs, and fragments of any such protein, including fragments obtained by digestion of the protein or a portion thereof, fragments obtained by expression of a gene coding for a portion of the amyloid precursor protein, and synthetic peptides having amino acid sequences corresponding to a portion of the amyloid precursor protein.

Amyloid precursor protein substrates for the assays of the present invention can be provided as a test reagent in a variety of forms. Although preferably derived from, or corresponding at least in part with the amino acid sequence of, APP 695, derivatives or analogs of other amyloid precursor protein isoforms are contemplated for use in the present method as well. APP 695 can be obtained by biochemical isolation or purification from natural sources such as described in Schubert, et al., *Proceedings of the National Academy of Sciences (USA)*, 86:2066 (1989); or by expression of recombinant DNA clones encoding the protein or a functional protein thereof. Knops, et al., *Journal of Biological Chemistry,* 266:7825 (1991).

The fragments of the amyloid precursor protein will comprise a sequence of amino acids sufficient of rrecognition and cleavage by the proteases of the present invention. Isolation of amyloid precursor protein from biological material usually will involve purification by conventional techniques such as chromatography, particularly affinity chromatography. Purified amyloid precursor protein or fragments thereof can be used to prepare monoclonal antibodies or polyclonal antibodies which can then be used in affinity purification according to conventional procedures.

Such an inhibition assay includes a method for determining whether a protein sequence is a functional substrate of the human amyloid precursor protein protease of the instant invention, said method comprising contacting a functional human amyloid precursor protein protease of the instant invention with said protein sequence, monitoring proteolysis activity by physically detectable means, and then identifying those substances which effect a chosen response.

A variety of convenient methods are applicable to the detection of proteolytic cleavage of the amyloid precursor protein substrate in the presence of a test sample. Several of the presently more preferred methods are described below, however, it will be recognized by the skilled worker in the field that many other methods can be applied to this step without departing from the inventive features thereof. In general, any method can be used for this purpose which is capable of detecting the occurrence of proteolytic cleavage of the amyloid precursor protein substrate. Such can be afforded by appropriate design of the amyloid precursor protein substrate such that cleavage produces a signal producing species, e.g., an optically responsive product such as a colored ro fluorescent dye.

Another principal approach involves the sensitive detection of one or more cleavage products such as by immunoassay. Presently, such cleavage product is preferentially a C-terminal fragment of the amyloid precursor protein substrate. Any fragment which appears upon incubation with the proteases of the present invention can be the object of detection.

The detection of one or more cleavage products characteristic of the pathologic proteolytic activity can be accomplished in many ways. One such method involves the procedure commonly known as the Western blot. Typically, after incubation of amyloid precursor protein with a protease of the present invention, gel electrophoresis is performed to separate the components resulting in the reaction mixture. The separated protein components are then transferred to a solid matrix such as a nitrocellulose or nylon membrane. An antibody specific to a fragment characteristic of amyloid precursor protein degradation is then reacted with the components fixed to the membrane and detected by addition of a secondary enzyme-labeled antibody conjugate. The location of the resulting bound conjugate is developed with a chromogenic substrate for the enzyme label.

A variety of immunoassay formats which are amenable to currently available test systems can also be applied to the detection of amyloid precursor protein fragments. Typically, the amyloid precursor protein substrate will incubated with a amyloid precursor protein protease of the present invention. The resulting intact amyloid precursor protein is then rendered immobilized (such as by capture onto a solid phase), or alternatively, the amyloid precursor protein protease is incubated with an immobilized form of the amyloid precursor protein substrate. Proteolytic cleavage is then detected by reacting the immobilized amyloid precursor protein substrate with an antibody reagent directed to a portion of the amyloid precursor protein substrate which is cleaved from the amyloid precursor protein substrate, or which defines the cleavage site.

Capture or immobilization of the amyloid precurosr protein substrate can be accomplished in many ways. An antibody can be generated specific to an epitope of amyloid precursor protein which is not on the cleavable fragment. Such an antibody can be immobilized and used to capture or immobilize intact amyloid precursor protein. Alternatively, a ligand or hapten can be covalently attached to amyloid precursor protein and a corresponding immobilized receptor or antibody can be used to capture or immobilize amyloid precursor protein. A typical ligand/receptor pair useful for this purpose is biotin/avidin. Examples of haptens useful for this purpose are fluorescein and digitoxigenin.

The solid phase on which amyloid precursor protein substrate is immobilized or captured can be composed of a variety of materials including microtiter plate wells, test tubes, strips, beads, particles, and the like. A particularly useful solid phase is magnetic or paramagnetic particles. Such particles can be derivatized to contain chemically active groups that can be coupled to a variety of compounds by simple chemical reactions. The particles can be cleared from suspension by bringing a magnet close to a vessel containing the particles. Thus, the particles can be washed repeatedly without cumbersome centrifugation or filtration, providing the basis for fully automating the assay procedure.

Labels for the primary or secondary antibody reagent can be selected from those well known in the art. Some such labels are fluorescent or chemiluminsecent labels, radioisotopes, and more preferably, enzymes for this purpose are alkaline phosphatase, peroxidase, and β-galactosidase. These enzymes are stable under a variety of conditions, have a high catalytic turnover rate, and can be detected using simple chromogenic substrates.

Proteolytic cleavage of the amyloid precurusor protein substrate can also be detected by chromatographic techniques which will separate and then detect the amyloid precursor protein fragments. High performance liquid chromatography is particularly useful in this regard. In applying this technique, a fluorescently tagged amyloid precursor protein is prepared. After incubation with the protease of the present invention, the reaction mixture is applied to the chromatographic column and the differential rate of migration of fluorescent fragemtns versus intact amyloid precursor protein is observed.

The instant invention provides such a screening system useful for discovering agents which inhibit the cleavage of the human amyloid precursor protein proteases of the instant invention, said screening system comprising the steps of:

a) isolating a human amyloid precursor protein protease;
b) exposing said human amyloid precursor protein protease to a potential inhibitor of this protease;
c) introducing a suitable substrate; and
d) quantifying the amount of cleavage of the substrate, relative to a control in which no potential inhibitor has been added.

This allows one to rapidly screen for inhibitors of the human amyloid precursor protein proteases of the instant invention. Utilization of the screening system described above provides a sensitive and rapid means to determine compounds which inhibit the proteases of the instant invention. This screening system may also be adapted to automated procedures such as a Pandex® (Baxter-Dade Diagnostics) system allowing for efficient high-volume screening of potential therapeutic agents.

In such a screening protocol a human amyloid precursor protein protease is prepared as elsewhere described herein, preferably using recombinant DNA technology. A sample of a test compound is then introduced to the reaction vessel containing the human amyloid precursor protein protease followed by the addition of an appropriate substrate. In the alternative the substrate may be added simultaneously with the test compound.

EXAMPLE 1

Purification of Human Amyloid Precursor Protein Protease by Ion-Exchange Chromatography As the proteases of this invention are serine proteases may be purified by known means. See, e.g., European Patent Application 569,777 A2, published Nov. 18, 1993.

(i) Sub-cellular fractionation. After expression of a gene product of the present invention in an appropriate cell line, the pelleted cells are frozen and then thawed to lyse the cells. If further lysing is necessary the cell pellet may be suspended in a buffer such as 0.32 M sucrose and then homogenized in batches using a 100 ml Elvehjem glass teflon potter (ten return strokes). The combined homogenate is centrifuged at 1000 g×10 minutes.

The loose pellet is removed, re-homogenized and centrifuged as described above. The supernatant from each extraction is combined and centrifuged at 15,000×g for 30 minutes. The resulting "P-2 pellet" is resuspended in 100 ml of ice-cold 0.32 M sucrose by vortexing and stored at −70° C. The supernatant from the last spin is centrifuged at 105,000×g for 60 minutes to yield the supernatant or soluble fraction ("S") and the microsomal fraction ("M") which is resuspended in 60 ml of 0.32 M sucrose. Both S and M are stored at −70° C.

(ii) Solubilization. The P-2 or M subfractions are solubilized by adjusting to the following conditions: 2% (w/v) Triton X-100 containing 50 mM Tris HCl buffer, pH 7.5. After stirring at 4° C. for 3.5 hours, the suspensions are centrifuged at 105,000×g for 60 minutes. The following final protein concentrations are used in solubilization: for P-2 (3.0 to 4.0 mg/ml); and for M (1.4 to 1.6 mg/ml). Solubilized supernatants are stored at −70° C. for later use. The soluble fraction is not treated with detergent but rather is adjusted to 50 mM in Tris HCl, pH 7.5, by the addition of stock 1 M buffer.

(iii) Ion-exchange chromatography. Chromatography is performed using a Gilson gradient liquid chromatograph (model 305 and 306 pumps) equipped with a 50 ml Rheodyne stainless steel loop injector model 7125, and connected to a MONO Q HR 10/10 COLUMN™ (Pharmacia, Piscataway, N.J.). Absorbance of column effluent is monitored at 280 nm.

Protein fractions of P-2, microsomal (M), or soluble (S) are loaded onto the column and equilibrated with 50 mM Tris HCl, pH 7.5 (conductivity 1.8 mU at 4° C.) at a flow rate of 2 ml/minute. The column is then washed with an equilibration buffer until the A280 nm in the eluent decreased to zero whereupon the column flow rate is increased to 4 ml/minute. Proteins are eluted as follows:

Solvents:
A=50 mM Tris HCl, pH 7.5
B=50 mM Tris HCl, pH 7.5, 1 M NaCl
Program:
0–50% B over 70 minutes
hold 50% for 10 minutes
50–100% B over 10 minutes
hold 100% B for 10 minutes
re-equilibrate Four milliliter fractions are collected throughout chromatography. The following protein loads are applied per column run:

P-2, 97 mg

S, 65 mg

M, 35 mg

In the initial studies, eluted fractions are monitored for A280, total protein (Bradford assay), and peptidase activity (as described infra). Pools made on the basis of peptidase activity are then prepared and then tested for their capactiy to process CHO cell derived APP C-terminally.

In all further studies, however, eluted fractions are also individually tested for their capacity for C-terminal processing of recombinant APP derived by baculovirus-directed expression.

EXAMPLE 2

Purification of Human Amyloid Precursor Protein Protease by Affinity Chromatography After sub-cellular fractionation and solubilization as described in Example 1, soluble (230 mg), P-2 (216 mg) or microsomal fraction (47 mg) are applied to a column of aprotinin sepharose, previously equilibrated with 20 mM Tris HCL, pH 7.0. Once loaded the column is washed with equilibration buffer (100 ml) and then eluted with 60 ml of 50 mM sodium acetate, pH 5.0, containing 500 mM sodium chloride. The flow rate is 1.0 ml/minute throughout.

Eluted fractions are monitored at 280 nm, analysed using the Bradford protein assay, and examined for APP C-terminal processing activity as described infra.

Active fractions from the aprotinin-sepharose chromatography may then be dialyzed against 50 mM Tris HCl, pH 7.5, and then subjected to ion-exchange chromatography over a MONO Q COLUMN™ as described in Example 1.

EXAMPLE 3

In Vitro Assay for Human Amyloid Precursor Protein Protease and Inhibitors Thereof An in vitro assay is developed which enables high throughput screening of sequences which are capable of serving as substrates for the protease of this invention. This high throughput assay also serves as an initial screen for compounds or compositions which have activity as inhibitors of the serine protease of this invention.

One preferred technology utilizes dansylated peptide substrates, in conjunction with subsequent detection of fluorescent peptide products by reverse phase high performance liquid chromatography, and post column fluorescence detection.

A fluorescently labeled dodeca-peptide substrate containing the same amino acid as observed surrounding the N-terminal region of the beta amyloid peptide sequence of human amyloid precursor protein is prepared by solid phase peptide synthesis using a commercially available peptide synthesizer, as described supra. Usually the peptides are cleaved an deprotected in 90% trifluoroacetic acid, 4% thioanisole, 2% ethanedithiol, and 4% liquified phenol for about two hours at ambient temperatures. In order to avoid unrelated carboxy digestion due to non-specific exoproteases present in all but the most highly purified protein preparations, a preferred substrate to employ is N-dansyl-Ile-Ser-Glu-Val-Met-Asp-Ala-Glu-Phe-Arg-His-Asp-Asp-Asp-Asp which is hereinafter identified as SEQ ID NO:9.

Aliquots of column fractions described in Example 1 are incubated with 10 μl of a reaction mixture so as to achieve the final component concentrations: test peptide of SEQ ID NO:9 (50 μM), captopril (300 μm), in a cocktail buffer comprising 100 mM in each of MES, Tris, and acetate, pH 6.5.

Incubation with ion-excahnge fractions is performed at 37° C. for about 24 hours, after which reactons are terminated by adjusting to 3% (v/v) final in trifluoroacetic acid.

HPLC analysis is performed usng a binary solvent delivery system with an auto injector system. Fluorescence detection is performed using a standard fluorometer (excitation at 310–410 nm, emission at 480–520 nm).

Aliquots of the above acidified incubation mixtures are injected onto a reverse phase chromatography column [Hypersil 5 μM C18 column (100×4.6 mm) fitted with a C18 5 μM guard column]. Isocratic spearation is achieved using 100 mM sodium acetate buffer, pH 6.5, containing 27% (v/v) acetonitrile. Identifiecation and quantification of resolved metabolites is made possible by comparison with the migration of synthetic peptide products, the structure of which are confirmed by PTC-amino acid analysis and fast atom bombardment mass spectrometry. One example of such a standard table is depicted in Table IV, infra.

TABLE IV

| Peptide (N-dansyl-) | HPLC retention time (minutes) | Cleavage Site |
|---|---|---|
| ISEVKMDAEFRHDDDD | 2.228 ± 0.024 | Substrate |
| ISEVKM | 5.398 ± 0.919 | Met-Asp |
| ISEVK | 3.413 ± 0.004 | Lys-Met |
| ISEV | 2.692 ± 0.003 | Val-Lys |
| ISE | 2.135 ± 0.002 | Glu-Val |
| IS | 4.412 ± 0.019 | Ser-Glu |

This table is derived from P. Tamburini, et al., European Patent Application Publication 0 569 777 A2, published Nov. 18, 1993. In all the experiments the HPLC column is calibrated for daily variation in the retention times of the enzymatically-generated products by analysis of synthetic product standards in parallel with the experimental samples. Data for the proteolytic metabolite profile of individual ion-exchange fractions is collected using commercially available software.

Once the reaction conditions are established, the proteolytic assays are then repeated using varying amounts of each of the test compounds believed to have proteolytic inhibitory activity. The results generated with these experiments, when compared with the controls in which no inhibitor is added, allow for the computation of an amount of a test compound effective in inhibiting 50% of the protease activity ($IC_{50}$).

EXAMPLE 4

In Vivo Assay for Human Amyloid Precursor Protein Protease and Inhibitors Thereof An in vivo assay, whereby specific sequences cleaved by the proteases of the present invention as well-as compounds inhibiting the proteases of the present invention may be defined, was developed essentially as described in T. A. Smith and B. D. Kohorn, Proceedings of the National Academy of Sciences (USA), 88:5159–5162 (1991).

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See. e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab$_2$',and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g., C. Milstein, *HANDBOOK OF EXPERIMENTAL IMMUNOLOGY*, (Blackwell Scientific Pub., 1986); J. Goding, *MONOCLONAL ANTIBODIES: PRINCIPLES AND PRACTICE*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., *Science* 242:423–426 (1988); PCT Publication No. Wo 88/01649, which was published Mar. 10, 1988; U.S. Pat. No. 5,260,203, issued Nov. 9, 1993, the entire contents of which are herein incorporated by reference. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of human amyloid precursor protein proteases.

In addition to being functional as direct therapeutic and diagnostic aids, the availability of a family of antibodies which are specific for the human amyloid precursor protein protease enables the development of numerous assay systems for detecting agents which bind to this receptor. One such assay system comprises radiolabeling human amyloid precursor protein protease-specific antibodies with a radionuclide such as $^{125}$I and measuring displacement of the radiolabeled human amyloid precursor protein protease-specific antibody from solid phase human amyloid precursor protein protease in the presence of a potential antagonist.

Numerous other assay systems are also readily adaptable to detect agents which bind human amyloid precursor protein protease. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the human amyloid precursor protein protease, this invention also provides antibodies which are specific for the hypervariable regions of the anti-human amyloid precursor protein protease antibodies. Some such anti-idiotypic antibodies would resemble the original epitope, the human amyloid precursor protein protease, and, therefore, would be useful in evaluating the effectiveness of compounds which are potential antagonists, agonists, or partial agonists of the human amyloid precursor protein protease. See, e.g., Cleveland, et al., *Nature* (*London*), 305:56 (1983); Wasserman, et al., *Proceedings of the National Academy of Sciences* (*USA*), 79:4810 (1982).

In another embodiment, this invention encompasses pharmaceutical formulations for parenteral administration which contain, as the active ingredient, the anti-human amyloid precursor protein protease antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 1089 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GAATTCCGGT TTTTTTTTTT TGAGGGTTTT GTGTTTCTTT ATTTGTTTTG GTTTTAGGTC      60

TTTACCAATT TGATTGGTTT ATCAACAGGG CATGAGGTTT AAATATATCT TTGAGGAAAG     120

GTAAAGTCAA ATTTGACTTC ATAGGTCATC GGCGTCCTCA CTCCTGTGCA TTTTCTGTTG     180

GAAGCACACA GTTAATTAAC TCAGTGTGGC GTTAGCGATG CTTTTTCATG GTGTCATTTA     240

TCCACTTGGT GAACTTGCAG ACTTGAGTGT AGACTCCTGG GTCATTGGGT TGGCCGCAAG     300

GGAAAGTTCC CCAGGACACC AGACCTTGCA GGGTACCTCT GCACACCAAC GGTCCCCCTG     360

AGTCACCATT GCAGGCGTTT TTCTTGGAGT CGGGGATGCC AGCGCACAGC ATGGAATTTT     420

CCAGTAAGTC CTTGTAAACC TTCGTGCAGT CCTGGGGGGA GATGAGCTTG ACATCCACGC     480

ACATGAGGTC AGAGGGAAAG GTCACATCTG GGCTCGTGGT AGTGCCCCAG CCGGAGACAG     540

TACAGGTGGT TCCAGGGGGT TCGCAGCGGG AGGGCAGCCT GACTTTCTTC ACCATGGATG     600

ACAGCCTGGC CTGGCTATTG AGCTTCACGA GCATGAGGTC ATTAACATGG GTCTGTGTGG     660

AGTAGCCGGG GTGGCGGAAT GACTTCGAGG CCTTGATCCT CTGAGCTCTC CTGTCGCCCA     720

GCGTATCACT GCCCAGGTGC ACGGTGTACT CATTCATCTT GCAGTGGGCG GCAGTGAGCA     780

CCCAGCGCTC ATTGACCAGG ACGCCTCCGC AGTGGAGCTG ATTGCCACTG AGCAGGGCCA     840

CCTGCCATGG GTGGGAGCCT CTTGCACATG GGGCGCCATC AATAATCTTG TCACCCTGGG     900

CTTCTTCTCC TGCAGTTTCC AAGGCTAAGG ATAGCAGTAA GATCTGCAGG GGCAGGAGAA     960

GGGATCTTGC CATGGTGCCC TGCTGAGCCG CTCAGGGGCT GCCAGGCGAG GAAGGGCCTC    1020

TCCTGCTGGA GCTCGAGAGG ATCTGATGTG ATCCAAGTTC CGACTTGGGC TGGCACACAC    1080

CGGAATTCC                                                            1089
```

(2) INFORMATION FOR SEQ ID NO:2:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Arg Ser Leu Leu Leu Pro Leu Gln Ile Leu Leu Ser Leu
1               5                   10                  15

Ala Leu Glu Thr Ala Gly Glu Glu Ala Gln Gly Asp Lys Ile Ile Asp
            20                  25                  30

Gly Ala Pro Cys Ala Arg Gly Ser His Pro Trp Gln Val Ala Leu Leu
            35                  40                  45

Ser Gly Asn Gln Leu His Cys Gly Gly Val Leu Val Asn Glu Arg Trp
50                      55                  60

Val Leu Thr Ala Ala His Cys Lys Met Asn Glu Tyr Thr Val His Leu
65                  70                  75                  80

Gly Ser Asp Thr Leu Gly Asp Arg Arg Ala Gln Arg Ile Lys Ala Ser
                85                  90                  95

Lys Ser Phe Arg His Pro Gly Tyr Ser Thr Gln Thr His Val Asn Asp
            100                 105                 110

Leu Met Leu Val Lys Leu Asn Ser Gln Ala Arg Leu Ser Ser Met Val
        115                 120                 125

Lys Lys Val Arg Leu Pro Ser Arg Cys Glu Pro Pro Gly Thr Thr Cys
130                 135                 140

Thr Val Ser Gly Trp Gly Thr Thr Thr Ser Pro Asp Val Thr Phe Pro
145                 150                 155                 160

Ser Asp Leu Met Cys Val Asp Val Lys Leu Ile Ser Pro Gln Asp Cys
                165                 170                 175

Thr Lys Val Tyr Lys Asp Leu Leu Glu Asn Ser Met Leu Cys Ala Gly
            180                 185                 190

Ile Pro Asp Ser Lys Lys Asn Ala Cys Asn Gly Asp Ser Gly Gly Pro
            195                 200                 205

Leu Val Cys Arg Gly Thr Leu Gln Gly Leu Val Ser Trp Gly Thr Phe
        210                 215                 220

Pro Cys Gly Gln Pro Asn Asp Pro Gly Val Tyr Thr Gln Val Cys Lys
225                 230                 235                 240

Phe Thr Lys Trp Ile Asn Asp Thr Met Lys Lys His Arg
                245                 250
```

(2) INFORMATION FOR SEQ ID NO:3:

(i) SEQUENCE CHARACTERISTICS:
(A) LENGTH: 1089 base pairs
(B) TYPE: nucleic acid
(C) STRANDEDNESS: single
(D) TOPOLOGY: linear (ii) MOLECULE TYPE: mRNA (xi) SEQUENCE DESCRIPTION: SEQ ID NO:3:

```
GAAUUCCGGU UUUUUUUUU UGAGGGUUUU GUGUUUCUUU AUUGUUUUG GUUUUAGGUC     60

UUUACCAAUU UGAUUGGUUU AUCAACAGGG CAUGAGGUUU AAAUAUAUCU UUGAGGAAAG   120

GUAAAGUCAA AUUUGACUUC AUAGGUCAUC GGCGUCCUCA CUCCUGUGCA UUUUCUGUUG   180

GAAGCACACA GUUAAUUAAC UCAGUGUGGC GUUAGCGAUG CUUUUUCAUG GUGUCAUUUA   240

UCCACUUGGU GAACUUGCAG ACUUGAGUGU AGACUCCUGG GUCAUGGGGU UGGCCGCAAG   300

GGAAAGUUCC CCAGGACACC AGACCUUGCA GGGUACCUCU GCACACCAAC GGUCCCCCUG   360

AGUCACCAUU GCAGGCGUUU UUCUUGGAGU CGGGGAUGCC AGCGCACAGC AUGGAAUUUU   420
```

-continued

| | | | | | |
|---|---|---|---|---|---|
| CCAGUAAGUC | CUUGUAAACC | UUCGUGCAGU | CCUGGGGGGA | GAUGAGCUUG ACAUCCACGC | 480 |
| ACAUGAGGUC | AGAGGGAAAG | GUCACAUCUG | GGCUCGUGGU | AGUGCCCCAG CCGGAGACAG | 540 |
| UACAGGUGGU | UCCAGGGGGU | UCGCAGCGGG | AGGGCAGCCU | GACUUUCUUC ACCAUGGAUG | 600 |
| ACAGCCUGGC | CUGGCUAUUG | AGCUUCACGA | GCAUGAGGUC | AUUAACAUGG GUCUGUGUGG | 660 |
| AGUAGCCGGG | GUGGCGGAAU | GACUUCGAGG | CCUUGAUCCU | CUGAGCUCUC CUGUCGCCCA | 720 |
| GCGUAUCACU | GCCCAGGUGC | ACGGUGUACU | CAUUCAUCUU | GCAGUGGGCG GCAGUGAGCA | 780 |
| CCCAGCGCUC | AUUGACCAGG | ACGCCUCCGC | AGUGGAGCUG | AUUGCCACUG AGCAGGGCCA | 840 |
| CCUGCCAUGG | GUGGGAGCCU | CUUGCACAUG | GGGCGCCAUC | AAUAAUCUUG UCACCCUGGG | 900 |
| CUUCUUCUCC | UGCAGUUUCC | AAGGCUAAGG | AUAGCAGUAA | GAUCUGCAGG GGCAGGAGAA | 960 |
| GGGAUCUUGC | CAUGGUGCCC | UGCUGAGCCG | CUCAGGGGCU | GCCAGGCGAG GAAGGGCCUC | 1020 |
| UCCUGCUGGA | GCUCGAGAGG | AUCUGAUGUG | AUCCAAGUUC | CGACUUGGGC UGGCACACAC | 1080 |
| CGGAAUUCC | | | | | 1089 |

We claim:

1. An isolated polynucleotide encoding a polypeptide functional as a human amyloid precursor protein protease which comprises the amino acid sequence as given by SEQ ID NO:2.

2. A composition comprising an isolated polynucleotide containing a sequence encoding a human amyloid precursor protein protease as claimed in claim 1, wherein said sequence encoding a human amyloid precursor protein protease is selected from the group consisting of:
   (a) SEQ ID NO:1;
   (b) SEQ ID NO:3; and
   (c) a polynucleotide complementary to (a) or (b).

3. A composition as claimed in claim 2 wherein the isolated polynucleotide is deoxyribonucleic acid.

4. A composition as claimed in claim 1 wherein the isolated polynucleotide is ribonucleic acid.

5. An expression vector capable of producing a human amyloid precursor protein protease in a host cell which comprises a polynucleotide as claimed in claim 2 in combination with regulatory elements necesssary for expression of the polynucleotide in the host cell.

6. An expression vector as claimed in claim 5 wherein the host cell is *Escherichia coli*.

7. An expression vector as claimed in claim 5 wherein the host cell is a mammalian cell line.

8. An expression vector as claimed in claim 5 which comprises the BK virus enhancer.

9. An expression vector as claimed in claim 8 which further comprises an adenovirus late promoter.

10. A transfected host cell harboring an expression vector as claimed in claim 5.

11. A transformed host cell as claimed in claim 10 which is *Escherichia coli*.

12. A transfected host cell as claimed in claim 10 which is a mammalian cell line.

13. A transfected host cell as claimed in claim 12 which is AV-12.

14. A method of evaluating the effectiveness of a test compound for the treatment of a condition associated with a deficiency of stimulation of a human amyloid precursor protein protease which method comprises:
   (a) introducing into a mammalian host cell an expression vector comprising DNA encoding a human amyloid precursor protein protease SEQ ID NO:2;
   (b) culturing said host cell under conditions such that the human amyloid precursor protein protease is expressed;
   (c) exposing said host cell expressing the human amyloid precursor protein protease to a test compound; and
   (d) measuring the change in a physiological condition known to be influenced by the activity of the human amyloid precursor protein protease relative to a control in which the transfected host cell is not exposed to the test compound.

15. A method of evaluating the effectiveness of a test compound for use in the treatment of conditions associated with an excess or deficiency of stimulation of a human amyloid precursor protein protease comprising the steps of:
   (a) isolating a human amyloid precursor protein protease SEQ ID NO:2;
   (b) exposing said isolated human amyloid precursor protein protease to the test compound;
   (c) exposing the isolated human amyloid precursor protein protease to a susceptible substrate simultaneously with or following the introduction of the test compound;
   (d) quantifying the concentration of susceptible substrate which has been proteolyzed; and
   (e) comparing the concentration of said proteolyzed susceptible substrate to a control in which no test compound were added.

16. A method of evaluating the effectiveness of a test compound for use in the treatment of conditions associated with an excess or deficiency of stimulation of a human amyloid precursor protein protease of SEQ ID NO:2 comprising the steps of:
   (a) introducing into a mammalian host cell a gene encoding an assayable gene product, said gene containing a region suitable for serving as a substrate for the human amyloid precursor protein protease of SEQ ID NO:2, said assayable gene product having a different phenotype depending on whether or not the region suitable for serving as a substrate for the human amyloid precursor protein protease is cleaved or not;
   (b) introducing into the mammalian host cell of step (a) an expression vector comprising DNA encoding a human amyloid precursor protein protease;

(c) culturing said host cell under conditions such that the human amyloid precursor protein protease and the assayble gene product are expressed;

(d) exposing said host cell expressing the human amyloid precursor protein protease to a test compound; and (e) assaying for the phenotype of the assayable gene product; and (f) comparing the phenotype of the assayable gene product to a control in which no test compound is added.

* * * * *

UNITED STATES PATENT AND TRADEMARK OFFICE
CERTIFICATE OF CORRECTION

PATENT NO. : 6,093,397
DATED : July 25, 2000
INVENTOR(S) : Eric P. Dixon, Edward M. Johnstone and Sheila P. Little It is certified that error appears in the above-identified patent and that said Letters Patent is hereby corrected as shown below:

Column 29,
Line 67, reads "...protease SEQ..." should read -- ...protease of SEQ... --

Column 30,
Line 38, reads "...protease SEQ..." should read -- ...protease of SEQ... --

Signed and Sealed this

Tenth Day of May, 2005

JON W. DUDAS
*Director of the United States Patent and Trademark Office*